United States Patent [19]

Niemi

[11] 4,053,743
[45] Oct. 11, 1977

[54] METHOD FOR CONTROLLING THE PH AND OTHER CONCENTRATION VARIABLES

[76] Inventor: Antti Johannes Niemi, Yrjo Liipolantie 5, Kauniainen, Finland

[21] Appl. No.: 658,897

[22] Filed: Feb. 18, 1976

[51] Int. Cl.² .................... G06F 15/46; G05D 11/08
[52] U.S. Cl. ............................. 364/500; 23/230 A; 364/105
[58] Field of Search .............. 235/151.12, 151.1, 150.1; 23/230 R, 230 A, 253 R, 253 A, 255 R, 255 E

[56] References Cited

U.S. PATENT DOCUMENTS

| | | | |
|---|---|---|---|
| 3,473,008 | 10/1969 | Bay et al. | 235/151.12 |
| 3,497,449 | 2/1970 | Urban | 235/151.12 X |
| 3,600,567 | 8/1971 | Varnela | 235/151.12 X |
| 3,614,682 | 10/1971 | Smith | 235/151.12 |
| 3,728,526 | 4/1973 | Youngblood | 235/151.12 X |

*Primary Examiner*—Joseph F. Ruggiero
*Attorney, Agent, or Firm*—Holman & Stern

[57] ABSTRACT

In a chemical reactor or analogous apparatus, a tank or similar system, pH and other concentration variables are controlled by a method wherein — when at least one desired outlet concentration or a function dependent on outlet concentrations is given — initially, the apparent output concentration of at least one feed component is calculated with the aid of the inlet concentration and the residence-time distribution; secondly, from the equilibrium dependencies on the basis of the values of said apparent output concentration and of each desired output concentration, or on the basis of a function dependent on the concentrations, there is calculated either the requisite apparent output concentration of each control component, or each physical control variable; thirdly, there is determined either the requisite feed concentration or flow of each control component with the aid of a control algorithm based on tion and the residence-time distributioned either the requisite feed concentration or flow of each control component with the aid of a control algorithm based on the residence-time distribution of said control component between its feed point and the outlet point of the reactor, or the control of each actuating variable that substantially affects a physical control, with the aid of an appropriate control algorithm; whereby other corresponding mathematical representations, e.g., time-variable and approximative representations are also considered as the said residence-time distributions, and the said residence-time distributions can also be equal and/or all but at least one of them can be replaced with a constant or flow-dependent time delay, or may even be overlooked; and finally, the corresponding control steps are effected. Said equilibrium dependences, from which the requisite apparent output concentration of each component is calculated, may preferably comprise a group of material balances and equilibrium equations, experimentally determined curves, or numerically expressed experimental dependences.

12 Claims, 4 Drawing Figures

METHOD FOR CONTROLLING THE PH AND OTHER CONCENTRATION VARIABLES

BACKGROUND OF THE INVENTION

1. Field of the Invention

The present invention relates to a method for controlling the pH and other concentration variables in a chemical reactor, an analogous apparatus, a tank or similar chemical system, particularly when at least one desired outlet concentration or a function dependent on outlet concentrations is given.

2. Description of the Prior Art

In industry, nature, the technological environment, and elsewhere there appear processes in connection with which the concentrations of the various components in the material to be treated change under the effect of chemical reactions or comparable physical phenomena. Some such analogous phenomena are dissolving, crystallization, and adsorption, when they are comparable to chemical reactions in regard to their mathematical treatment.

Rate of reaction. The rate at which the participating components are formed or spent is determined by the kinetic dependence characteristic of the reaction or respective phenomenon, by the concentrations of the components participating in the reaction, and by other variables and parameters, such as temperature, pressure, and the properties and concentration of the catalyst. The rate $r$ of a general irreversible reaction (1) is expressed, subject to certain limitations, by the dependence (2). The reaction formula (1) also links the quantitative changes in the various components to each other.

$$aA + bB + \ldots \rightarrow \text{products of reaction} \quad (1)$$

$$r = kC_A^a C_B^b \ldots \quad (2)$$

$a, b \ldots$ number of mass units (in moles) of component A, B, ... according to the basic reaction formula, $k$ rate coefficient of the reaction (depends on other process variables and parameters through which the progress of the reaction can be affected), $r$ rate of reaction (the rate of conversion of the component under observation in moles per volume unit), $C_A, C_B \ldots$ concentration of component A, B ... (in moles per volume unit).

The mathematic expression (2) expresses the rate of reaction at the point where the values of the concentrations and other process variables and parameters are given. It can also be used to describe the operation of a batch reactor provided with perfect mixing. In that case, representation in the form of a differential equation is obtained for the concentration of each component. This equation can generally be solved in cases corresponding to the various orders of kinetics [1].

[1] Campbell, D. C.: Process dynamics, Wiley 1958, pp. 256-7.

When considering a kinetic continuous flow reactor, a reaction rate term is added to the differential equation or partial differential equation expressing the momentary material balance at each point. A general method for solving the concentration of the component under consideration at different points in the reactor, including the outflow point, has not been presented. Some special cases are, however, mastered. If, for example, the reaction occurring in a continuous flow reactor is of first-order kinetics, the process is linear in regard to the concentration, and the kinetic term in itself does not complicate the solving of the equation. Owing to the linearity the superposition principle is valid and the kinetic term can be added to the flow and mixing characteristics, the latter having first been solved or determined experimentally [2].

[2] Levenspiel, O.: Chemical reaction engineering, Wiley 1962, pp. 254-9, 266, 282, 289-93.

A reversible reaction (3) proceeds simultaneously from the left to the right and from the right to the left, and each partial reaction has its own rate. The gross rate is obtained as the difference of the individual rates (4).

$$aA + bB + \ldots = mM + nN + \ldots \quad (3)$$

$$r = k_1 C_A^a C_B^b \ldots - k_2 C_M^m C_N^n \ldots \quad (4)$$

If all initial concentrations in a batch reactor are known, it is possible, if, for example, the concentration of A is selected as the variable, to express the concentrations of the other components by means of it and the initial concentrations and thereafter to solve how the reaction proceeds in time. Likewise, in regard to a continuous flow reactor, the concentration variables on the right side of the reaction formula (3) must also be taken into consideration, but otherwise the same applies to it as to the reactor discussed above, in which the reaction was irreversible.

Reaction equilibrium. A reaction (3) tends to an equilibrium at which its gross rate is zero, i.e., it proceeds at the same rate in each direction. The equilibrium constant K of the reaction can be determined according to the equation (4) as a ratio of the kinetic velocity coefficients [9]. In the expression of the equilibrium constant, and even elsewhere in this text, concentrations are used instead of the activities of the components. The activities can be replaced with concentrations especially in dilute solutions, and concentrations can even otherwise be reconverted to activities, provided that the dependences between the two are known. In a case of gaseous components, partial pressures can be used instead of concentrations.

[3] Ibid., pp. 12-3.

$$K = \frac{k_1}{k_2} = \frac{C_M^m C_N^n \ldots}{C_A^a C_B^b \ldots} \quad (5)$$

The values of the equilibrium constant, which is a function of temperature, pressure and other quantities, are known for a great number of reactions and can be obtained as such from literature or through the free energy of the reaction. If a complex mixture is in equilibrium, several equilibrium equations are satisfied simultaneously. Through them and the material balances which are here considered to include also the condition of electroneutrality, the state of equilibrium is completely determined. Analogous equilibrium dependences are valid not only for chemical reactions but also for many physicochemical and physical basic processes.

In fact, all chemical reactions and most comparable physical phenomena are reversible. In some cases the equilibrium constant, and thereby the concentration ratio corresponding to the equilibrium, has a very low or very high value. In such a case an assumption can be made concerning the irreversibility of the reaction, which approximate concept has already been applied above.

Often the reaction (3) proceeds in both directions at such a high rate that the equilibrium according to the equation (5) can be considered always valid at a point of observation, and kinetics need not be taken into consideration. Such a reaction is called in this discussion a fast reaction. Some suitable examples are the reactions between many inorganic acids and bases and their soluble salts in liquid phase and the reactions between many gaseous substances at high temperatures.

In practice the appearing chemical equilibrium cannot always be expressed by means of a clear chemical equation (e.g., (3)) or a group of such equations, or such a representation is not expedient. In such a case the use of equilibrium dependences, (e.g., (4)) expressed by means of simple formulas and parameters is out of question. On the other hand they can be expressed graphically, by means of curves, tables, or otherwise, without using mathematical analytical representation. Curves and respective means can be based on information obtained from literature, or they can be determined by laboratory tests or by measurements performed in the process. Some applicable examples are many processes used in the treatment of effluents; their chemistry may not be known in detail, but an interesting concentration variable or group of variables, as well as the factors essentially affecting it, may be measured.

Well known is, for example, the unambiguous dependence of H+ ion concentration, determined as a titer curve in equilibrium conditions in a laboratory and expressed by pH, on the quantity of the added chemical, acid or base, or on the ratio of the amounts of the chemicals. This is expressed conveniently as a curve, although the necessary calculations related to the reaction of a strong acid and a strong base, for example, can also be performed analytically. Corresponding curves can be drawn up for the concentrations of other ions as well. In a case of polyvalent acids or bases or in the presence of, for example, buffering components, the curves are more complicated. If in the reaction mixture there are several components which consume the reagent, curve diagrams or corresponding representations are used in order to take the effects of the various components into consideration.

Residence-time distribution. When describing the operation of an apparatus as a mixer, the discussion is usually limited to the dependence between the inlet and the outlet channels. The residence-time distribution expresses the probability with which the particles contained in the material element entering the apparatus at a given moment can be found in the outlet channel at each later moment. A change in the inlet concentration usually does not have any effect on the operation of the process as a mixer, but the process is usually linear in regard to the concentration. The residence-time distribution can be interpreted as the weighting function of the mixing process, and thus the outlet concentration can be calculated with the aid of it, the inlet concentration varying according to an arbitrary function of time [4]. When the process parameters are constant, a convolution integral (6) is used for the calculation. When the flow changes, the outlet concentration can be calculated with the aid of the time-variable residence distribution (7) [4]. In literature there are examples of theoretical [2, 4] numerically known residence-time distributions [5].

[2] Levenspiel, O.: Chemical reaction engineering, Wiley 1962, pp. 254–9, 266, 282, 289–93.
[4] Niemi, A.: Tracer testing of particulate matter systems for their dynamics, in Nuclear techniques in the basic metal industries, IAEA, Vienna 1973, pp. 136–9.
[5] Männistö, H., Niemi, A.: On the dynamics of a cellulose bleaching plant, in Radioisotope tracers in industry and geophysics, IAEA, Vienna 1967, pp. 371–84.

$$C_i(t) = \int_{-\infty}^{t} g(t - \theta) C_{in,i}(\theta) d\theta \qquad (6)$$

$$C_i(t) = \int_{-\infty}^{t} g(t,\theta) C_{in,i}(\theta) d\theta \qquad (7)$$

$g$ residence-time distribution (weighting function)
$C_i$ concentration of component $i$ in the outlet channel
$C_{in}$ inlet concentration
$t, \theta$ time variables The residence-time distribution/weighting function can be used to describe linear processes only. When kinetic reactors are considered, the residence-time distribution/weighting function can thus generally be used as a basis of the consideration of only a reactor in which a reaction of first-order kinetics occurs [2].

[2] Levenspiel, O.: Chemical reaction engineering, Wiley 1962, pp. 254–9, 266, 282, 289–93.

In special cases of mixing it has been possible to consider even other than first order reactions simultaneously with the mixing phenomenon. The reactors that can be considered in such cases are mainly only the plug-flow reactor and the stirred tank reactor with perfect mixing. In a plug-flow reactor the material elements entering simultaneously are considered to become immediately mixed with each other, but mixing does not occur between elements entering at different times. Since all elements have the same residence time or residence parameter value, the reactor does not have an actual residence-time distribution but this has degenerated into a constant delay time. Such a reactor can be considered substantially in the same manner as a batch reactor. An ideal mixing reactor, for its part, can be described by using an ordinary non-linear first-order differential equation or equation group, which can usually be solved at least numerically. The known functional form of the residence-time distribution is thus not utilized in connection with the solution.

Control: When a reactor is controlled in order to reach the desired outlet concentration, conventional feedback control is usually applied in practice. For reasons of measurement, the most common object of control is the pH, i.e., the H+(OH−) ion concentration, but even other concentration quantities are controlled in connection with continuous flow processes. Feedforward control is also applied in practice with the aim of compensating changes in the concentrations at the time they enter the process. The process models used in such cases are usually very simple. The follow-up control of combustion air in a constant proportion to the fuel feed is a suitable example of the control of the combustion reaction product, even though this follow-up control is not based on measuring the concentration. Sometimes a relatively simple feedforward circuit is used for pH control in connection with feedback control (see, e.g., [6]). The chemicals feed to a flotation process are controlled in some concentration plants so that they are in a constant proportion to the concentration of the incoming ore or the feed of the mineral component to be concentrated.

[6] Shinskey, F. G., Myron, T. J.: Adaptive feedback applied to feedforward pH control, in Advances in instrumentation 25, Paper No. 565–70, ISA, Pittsburgh 1970.

The analytical consideration of reactor dynamics and control has especially related to reactor dynamics and control has especially related to reactors with first-order kinetics. The ideal mixing reactor of the first order has been the principal object of interest (see, e.g., [7]). An exothermal ideal mixing reactor with first-order kinetics which is non-linear owing to the temperature dependence of the reaction rate coefficient has also been the object of keen theoretical interest [8]. Feedforward control of a first-order flotation reactor, using a model coupled parallelly to the process, has been suggested [9]. An example of optimal control of such a reactor is contained in, for example, [10].

[7] Solheim, O. A.: A guide to controlling cascaded chemical reactors, Control Engineering, July 1961, pp. 79–85.
[8] Oppelt, N., Wicke, E. (Ed.): Grundlagen der chemischen Prozessregelung, Oldenbourg 1964, pp. 46–125.
[9] Niemi, A.: A study of dynamic and control properties of industrial flotation processes, Acta Polyt. Scand. Chem. No. 48, Helsinki 1966, pp. 47–8.
[10] Niemi, A., Maijanen, J., Nihtilä, M.: Singular optimal feedforward control of flotation, IFAC Symp. on Optimization Methods, Varna, Bulgaria 1974-10-08 . . . 11.

Control of fast reactors in which the kinetics of the reactions can be left without consideration has in some cases been considered analytically. Thus, in [11] a method has been suggested for the control of a non-linear plug-flow reactor. Feedback control of an ideal stirred tank reactor in which likewise a fast non-linear reaction occurs is analyzed in [12, 13], and compared with an optimal control from a given initial state to the origin which problem is rarely encountered in practice, in [14]. In particular, poor mixing and the presence of buffering chemicals generally complicate obtaining acceptable results in, for example, pH control [6, 12 with references]. A satisfactory, generally applicable method for the consideration of a non-linear reactor with arbitrary flow characteristics and the control of the reactor has not yet been introduced.

[6] Shinskey, F. G., Myron, T. J.: Adaptive feedback applied to feedforward pH control, in Advances in instrumentation 25, Paper No. 565-70, ISA, Pittsburgh 1970.
[11] Talonen, T., Niemi, A.: Modelling of a pyrite smelting process, 4. IFAC Congress, Warsaw 1969, Session No. 66, pp. 141–55.
[12] Orava, J., Niemi, A.: State model and stability analysis of a pH control process, Int. J. of Control 20 (1974), pp. 557–67.
[13] Richter, J. D., Fournier, C. d., Ash, R. H., Marcikic, S.: Waste neutralization control, Instr. Technology 21 (1974) 4, pp 35–40.
[14] McAvoy, Th.J.: Time optimal and Ziegler-Nichols control, Ind. & Eng. Chemistry, Process Des. & Dev. 11 (1972), pp. 71–78.

SUMMARY OF THE INVENTION

The present invention povides a method of the character once described, which comprises calculating the apparent output concentration of the process material with the aid of the inlet concentration and the residence-time distribution, calculating the requisite apparent output concentration of each control component from the equilibrium dependences on the basis of the values of said apparent output concentration and of each desired output concentration, or on the basis of a function dependent on the concentrations, determining the requisite feed concentration or flow of each control component with the aid of a control algorithm based on the residence-time distribution of said control component between its feed point and the outlet point of the reactor, whereby other corresponding mathematical representations, such as time-variable and approximative representations are also considered as the said residence-time distributions, and the said residence-time distributions also can be equal, and all but at least one of them can be replaced with a constant or flow-dependent time delay or be overlooked, and effecting the corresponding control steps.

In an alternative embodiment there is calculated, instead of the requisite apparent output concentration of each control component as stated above, each physical control variable, whereby correspondingly, there is determined, not the requisite feed concentration or flow of each control component, but the control of each actuating variable that substantially affects a physical control, said determining taking place with the aid of an appropriate control algorithm.

Thus, this invention introduces a method for the mathematical consideration of a chemical reactor the mixing characteristics of which are arbitrary and in which the reaction equilibrium is reached or can be considered to be reached rapidly, and for the control of the reactor on the basis of this consideration. The method is considered to have a wide application especially in the process industries and in the treatment of supply and waste waters and solutions. It results in savings and an improvement in the quality of the process results and it can be easily and economically implemented using generally available equipment.

In the following the invention will be described as relating to a reactor, which here denotes a man-made or natural basin, tank or the like or a combination of such, and particularly to reactor control the purpose of which is to control the outlet concentration of a certain component or the combination of the outlet concentrations of several components in such a manner that it receives the desired value or changes in the desired manner. The concentration of one or more raw-material or other components to be fed into the reactor is assumed to change and thus be a disturbance variable with respect to control. The values of the said concentrations are known at the inlet point of the reactor through measurements effected at that point or prior to it. The reactor is controlled by means of a flow fed into it through this or some other point or, by means of the chemical concentration in this flow or, by means of several such flows or concentrations, or by means of thermal energy, pressure or a corresponding variable. The mixing characteristics of the reactor are of a general form and deviate normally from the simple basic types. Its residence-time distribution is assumed to be known, but the distribution need not have any known analytical expression and it can be known as a function of time or a corresponding variable, obtained through measurements. The essential components present in the reactor outflow are assumed to be in a thermodynamic equilibrium.

DESCRIPTION OF THE PREFERRED EMBODIMENTS

Figure 1:
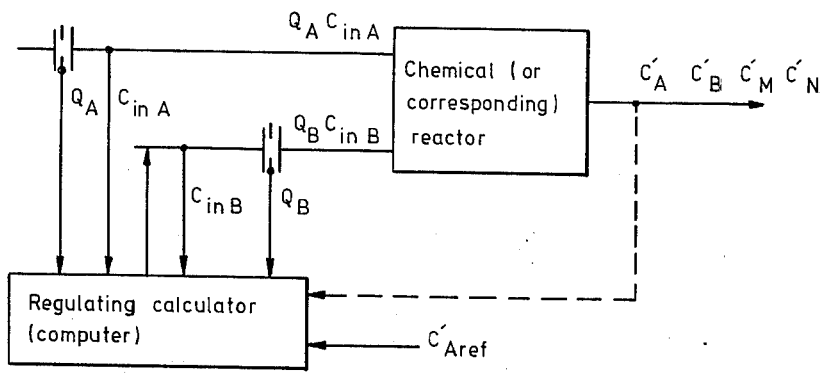
FIG. 1 is a diagram depicting the reactor, the flows and measurements connected with it, and the control device.

The method requires that, on the basis of the freely changing chemical concentration or concentrations and utilizing the known residence-time distribution of the process (6), the known apparent concentration or concentrations of said chemicals at the outlet point of the reactor are calculated without taking the reactions occurring in the apparatus into consideration. The inlet concentrations are assumed to be known, e.g., on the basis of concentration measurements prior to the reactor; $C_{inA}$ in FIG. 1. The total flow can be a known constant or a variable quantity; in the latter case the said apparent outlet concentration is calculated with the aid of the formula (7). The calculations provide for the total flow to be known through, for example, sufficient flow measurements. Since the residence-time distribution is normally known as a numerical function of time obtained by means of a tracer test, it is usually natural to perform the calculations numerically. On the other hand, the residence-time distribution can be estimated on the basis of experience and the construction of the apparatus and assumed to be sufficiently known when thus estimated.

By using the thus obtained apparent concentration value and the desired outlet concentration value, the required apparent final concentration of the control chemical is calculated next from the set of algebraic equations comprising the equilibrium equations and material balances (including the electroneutrality condition).

The following reaction in an aqueous solution is discussed as an example:

$$CH_3COOH + NaOH = CH_3COONa + H_2O \quad (8)$$

It is first assumed that NaOH is present in excess. The NaOH, and in an alkaline solution also $CH_3COOH$, is assumed to be completely dissociated. Also taking into consideration the known ion product $K_1$ of water, the following is obtained:

$$C_{NaOH} - C_{CH_3OOH} = C_{OH^-} - C_{H^+} \quad (9)$$

$$C_{H^+} \cdot C_{OH^-} = K_1 \quad (10)$$

If the objective of the control is to bring, for example, $C_{H^+}$, and the pH related to it, to a desired constant value, the required apparent concentration $C_{NaOH}$ of NaOH can easily be calculated from the above equations in spite of the buffering effect of $CH_3COOH$ in the feed flow.

If, on the contrary, acetic acid is present in excess, the concentration of undissociated acetic acid must be taken into consideration. The $CH_3COONa$ is assumed to be completely dissociated. The real final concentration of acetic acid is marked with a prime for the sake of clarity.

$$C_{CH_3COOH} - C_{NaOH} = C'_{CH_3COOH} + C_{H^+} - C_{OH^-} \quad (11)$$

$$\frac{C_{CH_3COO^-} \cdot C_{H^+}}{C'_{CH_3COOH}} = K_2 \quad (12)$$

$$C_{CH_3COOH} = C'_{CH_3COOH} + C_{CH_3COO^-} \quad (13)$$

In this case the following is obtained from the equations (11–13):

$$\frac{K_2/C_{H^+}}{1 + K_2/C_{H^+}} C_{CH_3COOH} - C_{NaOH} = C_{H^+} - C_{OH^-} \quad (14)$$

The objective of the control is now, e.g., to maintain the output concentration of $H^+$ and thus also $OH^-$) at a given constant value. By giving these concentrations the constant values in question in the equation (14) it is seen that the apparent output concentration of NaOH must be controlled as being linearly dependent on the apparent output concentration of $CH_3COOH$.

The case expressed by the equations (8, 10–13) is linear if the question is specifically of maintaining the output pH at a constant value in such a manner that changes in the inlet concentration of $CH_3COOH$ are compensated by regulating the inlet concentration of NaOH. If in the same case it is desired alternatively to maintain the $CH_3COO^-$ ion concentration at a constant value, a dependence is obtained between the concentrations of $CH_3COOH$ and NaOH, and this dependence is also linear with high accuracy. If the objective is, for example, to maintain the output concentration of undissociated $CH_{3COOH}$ at a constant value, the dependence is non-linear.

If the reaction mixture is more complicated than that described above, a larger set of equations is obtained but the presented calculation principle is retained. The object of control can naturally be any ion or chemical output concentration instead of pH. Even in the simplest cases pH control means the presence of at least two soluble compounds, except in a pure dilution process, so that the above calculation method is natural. The example also shows that the buffering chemicals can be included in the consideration. The measuring of the inlet concentration of acetic acid is essential, but it can also be determined through measuring the pH of the inlet flow by a conventional method and through further calculations by means of the known logarithmic dependence and, when necessary, also dissociation formulas (e.g., (12)).

Figure 2:
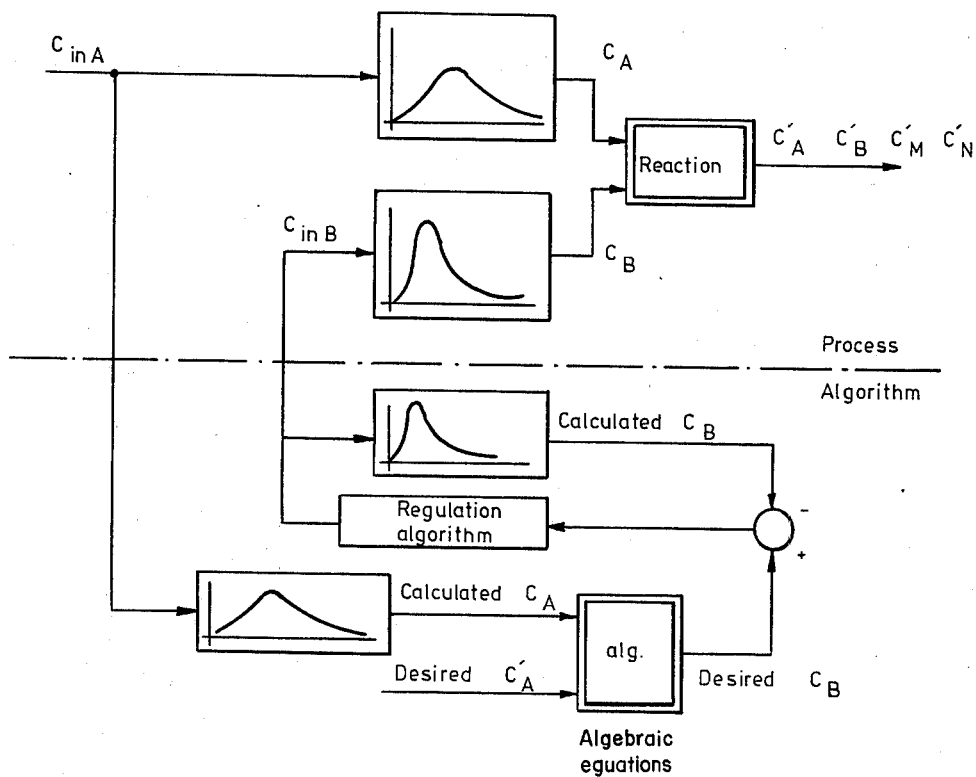
FIG. 2 is a diagram depicting a control algorithm and its connections with the process.
Figure 3:
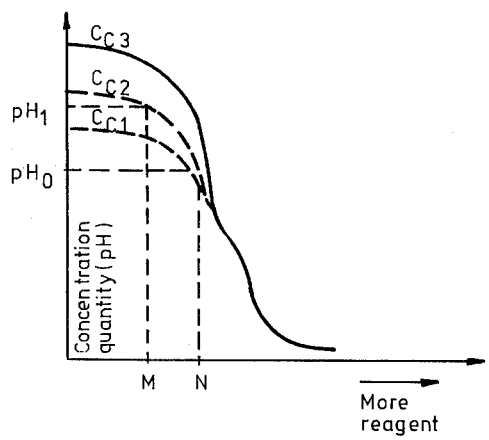
FIG. 3 depicts the effect, on a titration curve, of an additional component which spends reagent.

If the above representation methods are used in connection with a continuous flow reactor (FIGS. 1 and 2) when the chemical equilibrium dependence is known in the form of a curve or the like, the apparent output concentration of the process material is first calculated with the aid of its inlet concentration and residence-time distribution, using the convolution integral (6, 7). Let point M correspond to the obtained concentration value (FIG. 3). On the basis of the curve, the corresponding (ion) concentration or quantity related to it, such as $pH_1$, is obtained on the vertical axis. The distance between the point N on the horizontal axis, corresponding to the desired ion concentration value ($pH_0$), and the point $M_1$ directly or indirectly indicates the necessary reagent concentration, i.e., the apparent output concentration required of the reagent to be fed to the process.

To implement automatic control, the curve must be expressed by means of its analogous or numerical equivalent and the presented method respectively in a programmed form.

When the requisite apparent output concentration of the control chemical is known, several methods are available for calculating its feed concentration and for its physical control. FIG. 2 depicts one method of applying the principles of feedback control for determination of the feedforward control signal. In the FIGURE, $C_{inA}$ is the freely changing inlet concentration of the process, $C_A$ the corresponding apparent output concentration, and $C'_B$ its real output concentration. The symbols of the residence-time distributions have been drawn inside the flow process blocks, and the non-linear reaction treated as being momentary is included in the block provided with a double frame. The control device is normally a computer into which the value or time-domain function form of the desired output concentration of A, B, M, or other component is fed. The apparent output concentration of A is calculated by means of the measured inlet concentration and the known residence-time distribution, and when the said quantities are placed in an algebraic equation group, the requisite apparent output concentration of B can be calculated. It is compared with the apparent output concentration of B calculated with the aid of earlier $C_{inB}$ values and the known residence-time distribution, and the momentary value of $C_{inB}$ is calculated by means of an algorithm of feedback control, which can be any conventional PID control, the respective control step is effected. Either a measured or a calculated sequence of $C_{inB}$ data can be used for the calculation of $C_B$.

A more effective control algorithm is obtained by calculating with the aid of the formula (6) or (7) the effect of the measured $C_{inA}$ values on $C_A$ and further on the requisite $C_B$, even for future moments of time. The future values of $C_{inA}$ can then be given a value corresponding to the average operation point or they can be estimated by a suitable extrapolation method. On the other hand, the function $C_B$ is also calculated on the basis of previously measured $C_{inB}$ values and the future ones selected in the above manner, the momentary value of $C_{inB}$ being the quantity to be varied. The latter response is compared with the former and the momentary value of $C_{inB}$ is selected by adjusting the responses, for example, by the method of the least squares.

Figure 4:
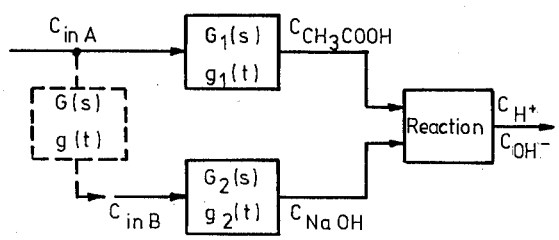
FIG. 4 is a diagram depicting a continuous flow reactor, its concentration variables, and its feedforward control.

When $C_B$ is known or can thus be extrapolated, there are even other control techniques available for controlling the $C_{inB}$. Especially in a linear case in the procedure next described, a normal operation point, i.e., the steady state in which all concentrations have their constant values corresponding to the desired state, is taken as the initial point of the observations, i.e., the new origin. This does not affect the accuracy of the following analysis, but can be used to simplify the analysis, since the constants to be summed up, particularly the right side of the equation (14), then need not be taken into consideration. By applying the Laplace transform, the following control principle is obtained (FIG. 4):

$$\Delta C_{inB}(s) = \frac{K_2/C_{H+}}{1 + K_2/C_{H+}} \cdot \frac{G_1(s)}{G_2(s)} \Delta C_{inA}(s) = \quad (15)$$

$$\frac{K_2/C_{H+}}{1 + K_2/C_{H+}} G(s) \Delta C_{inA}(s) \quad (16)$$

Here the notation $\Delta C_{inA}$ stands for the inlet concentration of $CH_3COOH$ and $\Delta C_{inB}$ for the inlet concentration of NaOH. A control method based on a similar formula has previously been presented in a general form in literature, in a form corresponding to analogous control [15], but its application to the control of the fact reactor has never been suggested. In order that it be possible to apply the method practically it must be assumed that the partial processes $g_1$ and $g_2$ can be expressed by simple, easily transformable analytical expressions. This is a considerable limitation, for the impulse responses or weighting functions normally deviate considerably from the ideal models. They are usually determined experimentally, by means of tracers, for example, and can be tabulated as data series on the basis of the measurements. If an attempt is made to apply analytical models mathematically to these results, considerable approximations are necessary, in which case the results obtained when further applying these models are also highly inaccurate.

[15] Koppel, L.B.: Introduction to control theory. Prentice-Hall, 1968. pp. 23-4, 27-9.

The new control algorithm to be presented is characterized in that the weighting functions or residence-time distributions, known in a numerical form, of the partial processes are used in determining the control function, without approximating them with any mathematically analytical expressions. The method is based on the use of the Fourier transform. The conditions of convergence of this transformation method are more restricting than the corresponding conditions of the Laplace transform, for example, but it can easily be shown that the concentration processes occurring in a continuous flow tank satisfy the conditions of the Fourier transform. Processes satisfying the same conditions abound in other fields of technology as well.

When the Fourier transform is applied to the convolution integral (6), the Fourier transform of the apparent outlet concentration is obtained as a product of the Fourier transforms of the weighting function and of the inlet concentration. The frequency response of a control device leading to a complete compensation is the ratio of the frequency responses of the parallel feedforward partial processes, and the weighting function of the control device is obtained from it by an inverse Fourier transform.

$$g(t) = \frac{K_2/C_{H+}}{1 + K_2/C_{H+}} F^{-1} \frac{G_1(j\omega)}{G_2(j\omega)} = \frac{K_2/C_{H+}}{1 + K_2/C_{H+}} \cdot \quad (16)$$

$$\frac{1}{\pi} \int_O^\infty \left( \frac{\alpha\gamma + \beta\delta}{\gamma^2 + \delta^2} \cos\omega t - \frac{\alpha\delta + \beta\gamma}{\gamma^2 + \delta^2} \sin\omega t \right) d\omega$$

in which $$\alpha = \int_O^\infty g_1(t)\cos\omega t\, dt \quad \beta = \int_O^\infty g_1(t)\sin\omega t\, dt \quad (17,18)$$

$$\gamma = \int_O^\infty g_2(t)\cos\omega t\, dt \quad \delta = \int_O^\infty g_2(t)\sin\omega t\, dt \quad (19,20)$$

The result resembles an expression derived in [5]; the coefficient term relating to the reaction, however, distinguishes the result also formally from that expression. In the said reference the transform was applied particularly to signals in order to analyze the unit process between them, and a novel feature of the method now introduced is the application of the transformation method to the weighting functions of real process units and to the ratio of their transforms in order to synthesize the control function. [5] Mannisto, H., Niemi, A.: On the dynamics of a cellulose bleaching plant, in Radioisotope tracers in industry and geophysics, IAEA, Vienna 1967, pp. 371-84.

The control function $g(t)$, together with the measured inlet functions $C_{inA}(t)$, can now be placed in an expression of the form (6) to calculate repeatedly the control function $C_{inB}(t)$. If the measurements and numerical calculations can be performed accurately, the control concentration can also be calculated accurately and thereby the compensation performed completely.

The presented method uses numerical process data and numerically known weighting functions, and restricting assumptions relating to their forms are not necessary. In practice, however, the control requires that the time parameters of the process $g_2$ are not greater than the parameters of the process $g_1$. This condition is usually satisfied automatically, for it is natural to feed the reagent to the process after the point where the inlet concentration is measured, or at that point at the earliest.

If, in the cases described as examples, the two residence-time distributions are equal, as is the case when the chemical flows have a common feed point, it is observed that in order to maintain the final concentration constant the $C_{inB}$ must be controlled in such a manner that the difference between the inlet concentrations remains unchanged. In a non-linear case the control is more complicated in spite of a possible equality of the flow characteristics.

Owing to the imperfection of the flow models, inaccuracies in the measurements, and secondary reactions the control can be supplemented with feedback circuits. Examples of linking conventional feedback control to feedforward control have been presented in the literature [6, 10]. In such a case the object of the measuring is the final outlet quality of the reactor, and the corresponding control component can be, for example, added to the control applied to the feed channel, which was calculated by means of the desired algorithm. [6] Shinskey, F. G., Myron, T. J.: Adaptive feedback applied to feedforward pH control, in Advances in instrumentation 25, Paper No. 565-70, ISA, Pittsburgh 1970. [10] Niemi, A., Maijanen, J., Nihtila, M.: Singular optimal feedforward control of flotation, IFAC Symp, on Optimization Methods, Varna, Bulgaria 1974-10-08 ... 11.

In practice the control of the inlet concentration is often implemented by controlling the flow in such a manner that the total flow $Q_B$ and thereby the product $Q_B C_{inB}$ is varied, the $C_{inB}$ remaining substantially unchanged. If the changes in the control flow are small in comparison with the main flow of the process, the presented calculation methods are applicable as such. If the $Q_B$ is not small, its effect as a changing parameter in the residence-time distributions must be taken into consideration (7).

The inlet and outlet channels can in some cases have a heterogeneous concentration. In such cases the residence-time distributions denote the processes between the feed and measuring connections, and the measuring and the control are applied to the respective local quantities.

The method is in principle applicable as such to cases in which even deviating demands are set on the control. Thus, instead of one outlet concentration, a combination of concentrations can be controlled, or the aim can be the optimization of the value of a criterion including the same quantities. There can be more than one control quantity, in which case respectively more than one outlet quantity can have a given target value. Furthermore, allowances can be made in regard to the number of the measurements, if the necessary quantities are otherwise known with a sufficient accuracy. If the residence-time distribution of the reactor or an essential part of the same is brought into the form of an analytical model, it can often be brought further into some other mathematical form which leads to the same or nearly the same apparent output concentration, and such a method must therefore be considered to belong to the scope of the presented residence-time distribution method.

Although the equilibrium constant has been indicated above as being invariable, its dependence on temperature, pressure, and other quantities can also be included in the consideration. The said quantities can be measured and taken into consideration in determining the corresponding value of K at each given moment, and the described algorithm of feedback control, for example, can be used for the control. In some cases it is also possible to include, for example, the generation of heat of reaction in the equation group and determine its effect on the temperature. Such a calculation has been performed for a batch reactor, and only for such a one, in [16]. Respectively, the heat effect, pressure, etc., can also be used as the control quantity.

[16] Niemi, A., Koskinen, T.: Simulation of the copper converter, Mineral Processing and Extractive Metallurgy 1968, pp. C 201-8.

What is essential in the method is that at least two residence-time distributions are involved in it, namely, that of the process material and that of the control chemical, which can deviate from each other, and at least one of them is used in the control calculations. It is also essential that when the material proceeds in the reactor the reactions occurring in it are not taken into consideration, contrary to reality, and they are considered as being transferred to the outlet point of the reactor, i.e., the mixing and the reactions are considered as being successive and not parallel. This is justified by the assumption of the reversibility and rapidity of the reactions, for which reason in a theoretical ideal case the form in which the participating components arrive at the point of observation has in principle no significance.

What is claimed is:

1. A method for controlling concentration variables of process material in a chemical reactor containing reactants which reach thermodynamic equilibrium substantially simultaneously, the reactor having at least one process inlet flow through the inlet, one process outlet flow through an outlet, and one control inlet flow, further at least one desired outlet concentration being provided, the method comprising the steps of:
   a. measuring the concentration of at least one reactant of the process material in the process inlet flow, and the concentration of a reactant of a control material in the control inlet flow;
   b. providing a residence-time distribution function for the process material flow from said inlet to said outlet, and a residence-time distribution function for the control material flow from said control inlet to said outlet;
   c. calculating an apparent outlet concentration of said at least one reactant of the process material and an apparent outlet concentration of said reactant of the control material with the aid of the respective measured inlet concentration and the respective residence-time distribution function in accordance with the following relationship:

$$C_i(t) = \int_{-\infty}^{t} g(t - \theta) C_{in,i}(\theta) d\theta \; ;$$

$g$ = residence-time distribution (weighting function)
   $C_i$ = concentration of component $i$ in the outlet channel
   $C_{in}$ = inlet concentration
   $t, \theta$ = time variables
   d. assuming thermodynamic equilibrium and utilizing said provided desired outlet concentration of the preamble as well as said apparent outlet concentration of said at least one reactant of the process material in step (c), calculating a desired apparent concentration of said reactant of the controlled inlet flow at said outlet; and
   e. controlling the control inlet flow by means of a feedback control, like a proportional, integral and derivative PID control, on the basis of the difference between said apparent outlet concentration of the control reactant in step (c) and said desired apparent outlet concentration of said control reactant in step (d).

2. The method according to claim 1 wherein the thermodynamic equilibrium from which the desired apparent outlet concentration of each reactant of the control inlet flow is calculated comprises a group of material balances and equilibrium equations.

3. The method according to claim 1 wherein the thermodynamic equilibrium from which the desired apparent outlet concentration of each reactant of the control inlet flow is calculated comprises experimentally determined dependencies.

4. The method according to claim 1 in which step (a) is carried out by measuring the pH of said process inlet flow from which is calculated the concentration.

5. A method for controlling concentration variables of process material in a chemical reactor containing reactants which reach thermodynamic equilibrium substantially simultaneously, the reactor having at least one process inlet flow through an inlet, one process outlet flow through an outlet, and one control inlet flow, further at least one desired outlet concentration being provided, the method comprising the steps of:
   a. measuring the concentration of at least one reactant of the process material in the process inlet flow;
   b. providing a residence-time distribution function for the process material flow from said inlet to said outlet, and a residence-time distribution function for the control material flow from said control inlet to said outlet;
   c. assuming thermodynamic equilibrium and utilizing said provided desired outlet concentration of the preamble, calculating a constant factor equivalent to the coefficient of linear dependence between the concentrations of the process and control reactant; and
   d. controlling the control inlet flow on the basis of the measured concentration of said reactant in step (a) multiplied by a control function, said control function being defined by its Laplace transformation being equivalent to the ratio of Laplace transformations of the residence-time distributions of the process material and of the control reactant in turn multiplied by said constant factor in step (c).

6. The method according to claim 5 wherein the thermodynamic equilibrium from which the desired apparent outlet concentration of each reactant of the control inlet flow is calculated comprises a group of material balances and equilibrium equations.

7. The method according to claim 5 wherein the thermodynamic equilibrium from which the desired apparent outlet concentration of each reactant of the control inlet flow is calculated comprises experimentally determined dependencies.

8. The method according to claim 5 in which step (a) is carried out by measuring the pH of said process inlet flow from which is calculated the concentration.

9. A method for controlling concentration variables of process material in a chemical reactor containing reactants which reach thermodynamic equilibrium substantially simultaneously, the reactor having at least one process inlet flow through an inlet, one process outlet flow through an outlet, and one control inlet flow, further at least one desired outlet concentration being provided, the method comprising the steps of:
   a. measuring the concentration of a least one reactant of the process material in the process inlet flow;
   b. providing a residence-time distribution function for the process material flow from said inlet to said outlet, and a residence-time distribution function for the control material flow from said control inlet to said outlet;
   assuming thermodynamic equilibrium and utilizing said provided desired outlet concentration of the preamble, calculating a constant factor equivalent to the coefficient of linear dependence between the concentrations of the process and control reactant; and
   d. controlling the control inlet flow on the basis of the measured concentration of said reactant in step (a) multiplied by a control function, said control function being defined by its Fourier transformation being equivalent to the ratio of Fourier transformations of the residence-time distributions of the process material and of the control reactant in turn multiplied by said constant factor in step (c).

10. The method according to claim 9 wherein the thermodynamic equilibrium from which the desired apparent outlet concentration of each reactant of the control inlet flow is calculated comprises a group of material balances and equilibrium equations.

11. The method according to claim 9 wherein the thermodynamic equilibrium from which the desired apparent outlet concentration of each reactant of the control inlet flow is calculated comprises experimentally-determined dependencies.

12. The method according to claim 9 in which step (a) is carried out by measuring the pH of said process inlet flow from which is calculated the concentration.

* * * * *